(12) United States Patent
Rogers et al.

(10) Patent No.: US 11,175,260 B2
(45) Date of Patent: Nov. 16, 2021

(54) ADJUSTING NANOPORE DIAMETER IN SITU FOR MOLECULE CHARACTERIZATION

(71) Applicant: International Business Machines Corporation, Armonk, NY (US)

(72) Inventors: Priscilla Racquel Rogers, Fitzroy (AU); James R. Kozloski, New Fairfield, CT (US)

(73) Assignee: International Business Machines Corporation, Armonk, NY (US)

(*) Notice: Subject to any disclaimer, the term of this patent is extended or adjusted under 35 U.S.C. 154(b) by 140 days.

(21) Appl. No.: 16/174,615

(22) Filed: Oct. 30, 2018

(65) Prior Publication Data
US 2020/0132624 A1    Apr. 30, 2020

(51) Int. Cl.
*G01N 27/447* (2006.01)
*G01N 33/487* (2006.01)
*B82Y 15/00* (2011.01)

(52) U.S. Cl.
CPC . *G01N 27/44791* (2013.01); *G01N 33/48721* (2013.01); *B82Y 15/00* (2013.01)

(58) Field of Classification Search
CPC ................ G01N 27/44791; G01N 33/48721
See application file for complete search history.

(56) References Cited

U.S. PATENT DOCUMENTS

| | | | |
|---|---|---|---|
| 6,706,203 B2 | 3/2004 | Barth et al. | |
| 7,638,034 B2* | 12/2009 | Sansinena | B82Y 15/00 205/775 |
| 8,256,293 B2 | 9/2012 | Rueger | |
| 8,450,198 B2 | 5/2013 | Lin et al. | |
| 8,951,727 B2* | 2/2015 | Jaramillo-Botero | G01N 27/44704 435/6.1 |
| 9,255,321 B2* | 2/2016 | Baldauf | C23C 14/12 |
| 9,605,307 B2* | 3/2017 | Chen | C12Q 2565/631 |
| 9,605,309 B2* | 3/2017 | Davis | G01N 27/44791 |
| 9,624,537 B2* | 4/2017 | Huber | G01N 21/6452 |

(Continued)

FOREIGN PATENT DOCUMENTS

| | | | |
|---|---|---|---|
| CN | 102901763 A | 1/2013 | |
| CN | 102901763 B | 6/2014 | |
| WO | WO-2013116509 A1 * | 8/2013 | ....... G01N 33/48721 |

OTHER PUBLICATIONS

J.K. Holt, Fast Mass Transport Through Sub-2-Nanometer Carbon Nanotubes, Science, May 19, 2006, p. 1034-37. (Year: 2006).*

(Continued)

*Primary Examiner* — Luan V Van
*Assistant Examiner* — Caitlyn Mingyun Sun
(74) *Attorney, Agent, or Firm* — Daniel M. Yeates (57) ABSTRACT

A nanopore device for molecular characterization that includes a supporting substrate. The supporting substrate has at least one nanopore where the nanopore is a carbon nanotube of a first diameter. The nanodevice is configured to provide a stimulus to the carbon nanotube causing the first diameter to change to a second diameter. The nanopore device also includes a device configured to apply the stimulus to the nanopore. The nanopore device further includes an electrical circuit configured to measure an electrical property across the nanopore, where there is a change in the electrical property when a molecule traverses the nanopore.

7 Claims, 7 Drawing Sheets

(56) References Cited

U.S. PATENT DOCUMENTS

| | | |
|---|---|---|
| 2013/0256137 A1 | 10/2013 | Holt |
| 2013/0256144 A1 | 10/2013 | Holt |
| 2013/0260472 A1* | 10/2013 | Holt ................ B82Y 40/00 436/149 |
| 2013/0309776 A1 | 11/2013 | Drndic et al. |
| 2014/0001110 A1 | 1/2014 | Lee et al. |
| 2014/0158540 A1* | 6/2014 | Ohura ............ G01N 27/44791 204/543 |
| 2014/0174927 A1 | 6/2014 | Bashir et al. |
| 2015/0259724 A1* | 9/2015 | Guan ............. G01N 33/48721 435/6.11 |

OTHER PUBLICATIONS

Vogel et al., "Quantitative Sizing of Nano/Microparticles with a Tunable Elastomeric Pore Sensor", Analytical Chemistry, 2011, Abstract Only, 2 pages.
Willmott et al., "Use of tunable nanopore blockade rates to investigate colloidal dispersions", J. Phys.: Condens. Matter, May 24, 2010, 19 pages.
Ito et al., "A Carbon Nanotube-Based Coulter Nanoparticle Counter", Acc. Chem. Res., 37, Publication Date (Web): Oct. 15, 2004, Abstract Only, 2 pages.

* cited by examiner

ADJUSTING NANOPORE DIAMETER IN SITU FOR MOLECULE CHARACTERIZATION

BACKGROUND

The present disclosure relates to molecule characterization, and more specifically, to characterizing multiple molecules of varying size with a tunable nanopore.

Identifying and characterizing chemicals and other products is an integral part of several industries. There are several techniques used to determine the makeup and characteristics of molecules and compounds including, but not limited to, gas chromatography, mass spectrometry, Fourier transform infrared spectroscopy, nuclear magnetic resonance spectroscopy, and calorimetry. Each characterization technique can provide specific information about the chemical compounds being characterized. A technique can be chosen based on the state (i.e. solid, liquid, gas) of the substance being tested and the properties that need to be determined.

SUMMARY

Aspects of the present disclosure are directed toward a nanopore device that includes a supporting substrate. The supporting substrate has at least one nanopore where the nanopore is a carbon nanotube of a first diameter. The nanodevice is configured to provide a stimulus to the carbon nanotube causing the first diameter to change to a second diameter. The nanopore device also includes a device configured to apply the stimulus to the nanopore. There is also an electrical circuit configured to measure an electrical property across the nanopore, where there is a change in the measure electrical property when a molecule traverses the nanopore.

Additional aspects of the present disclosure are directed toward a nanopore device similar to the nanopore device discussed above, where the nanopore includes at least one layer of graphene.

Additional aspects of the present disclosure are directed toward a method including submerging a nanopore device in a polydisperse solution, where the polydisperse solution includes an electrolyte and a molecule. The method further includes setting a first geometry of the nanopore small enough that the molecule cannot traverse through the nanopore. The method further includes applying a stimulus to the nanopore, where the stimulus causes a change to the second geometry, where the second geometry allows the molecule to traverse the nanopore. The method further includes detecting the first molecule based on a change in an electrical property. The method further includes characterizing the molecule based on the change in the electrical property.

The present Summary is not intended to illustrate each aspect of, every implementation of, and/or every embodiment of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of certain embodiments and do not limit the disclosure.

While the present disclosure is amenable to various modifications and alternative forms, specifics thereof have been shown by way of example in the drawings and will be described in detail. It should be understood, however, that the intention is not to limit the present disclosure to the particular embodiments described. On the contrary, the intention is to cover all modifications, equivalents, and alternatives falling within the spirit and scope of the present disclosure.

DETAILED DESCRIPTION

Characterization of substances has applications in several industries including, but not limited to, pharmaceuticals, chemical synthesis, materials science, and in all phases of industry from research and development to reverse engineering to medical diagnostics. One technique developed to characterize particles in fluids is resistive pulse sensing.

Resistive pulse sensing is a technique used to characterize particles dispersed in a fluid. Generally, the particles are dispersed in a conducting fluid. The fluid is sent through a small pore approximately the diameter of the particle to be characterized. A circuit is arranged such that the conducting fluid provides a path for current to flow through the pore. When a particle passes through the pore, it displaces the fluid and thereby reduces the electric current flow through the pore, thereby causing a spike in voltage due to an increase in electrical resistance across the pore. The relative size of the change in voltage correlates to the size of the particle.

Embodiments of the present disclosure are directed toward particle characterization, and, more specifically, to the characterization of individual particles in a polydisperse sample using in situ tunable nanopores. In these embodiments, the nanopores are derived from materials that can be configured to have pores on a nanoscale, such that they can characterize individual molecules, and such that they are tunable. Some examples of adequate materials are graphene and carbon nanotubes.

Embodiments of the present disclosure recognize characterization of a single molecule necessitates a pore that is essentially the same size as a molecule. Thus, embodiments of the present disclosure utilize materials that may be modified into pores on a nanoscale. For purposes of this application, all pores are considered nanopores and the term pore and nanopore may be used interchangeably.

Embodiments of the present disclosure recognize a nanopore of fixed size can be the limiting factor in characterizing particles of different sizes in a polydisperse sample. If the particle is too big, it cannot traverse the pore. If the particle is too small, it cannot displace enough fluid to cause a noticeable change in the electrical resistance. Embodiments of this disclosure provide for nanopores that can be adjusted (e.g., tuned) in situ. Thus, a tunable nanopore can improve molecular characterization by limiting the scenarios in which nanopore size is the limiting factor in characterization.

Embodiments of the present disclosure recognize that the resistive pulse sensing technique has limited capability to characterize different particles in a polydisperse sample (e.g., a sample with multiple, chemically distinct particles). Because particles of a certain size can only be sensed and characterized in pores of a similar size, a system containing only one nanopore size cannot be used to characterize multiple molecules of differing size in the same sample. Thus, resistive pulse sensing using fixed-size pores is most effective for determining if a target particle is present in a sample, or in situations where there is some foreknowledge of the particle size prior to a characterization attempt. Otherwise, using resistive pulse sensing with fixed-size pores becomes a process of trial and error.

Embodiments of the present disclosure recognize the usefulness of a tunable nanopore that can be modified in situ. Accordingly, embodiments of the present disclosure can provide a tunable nanopore that can be utilized in resistive pulse sensing applications. One nanopore can be used to characterize multiple particles of diverse sizes in a single sample. Embodiments of this disclosure provide for a tunable nanopore that can be dynamically modified in situ based on an algorithm to characterize and determine particles of unknown species or size. In some embodiments the algorithm is a directed search algorithm. For purposes of this application, the terms algorithm and directed search algorithm may be used interchangeably. The initial size of the nanopore can be set such that no particle in the sample can traverse the pore. The nanopore can be dynamically altered in situ, causing a change in pore size such that particles begin to traverse the nanopore and can be detected and characterized. This can continue until a maximum nanopore sized is reached and multiple particles of different sizes have been characterized. Nanopore sizes can range from about 1 to about 1000 nm in diameter.

The aforementioned advantages are example advantages, and embodiments exist that can contain all, some, or none of the aforementioned advantages while remaining within the spirit and scope of the present disclosure.

Figure 1A:
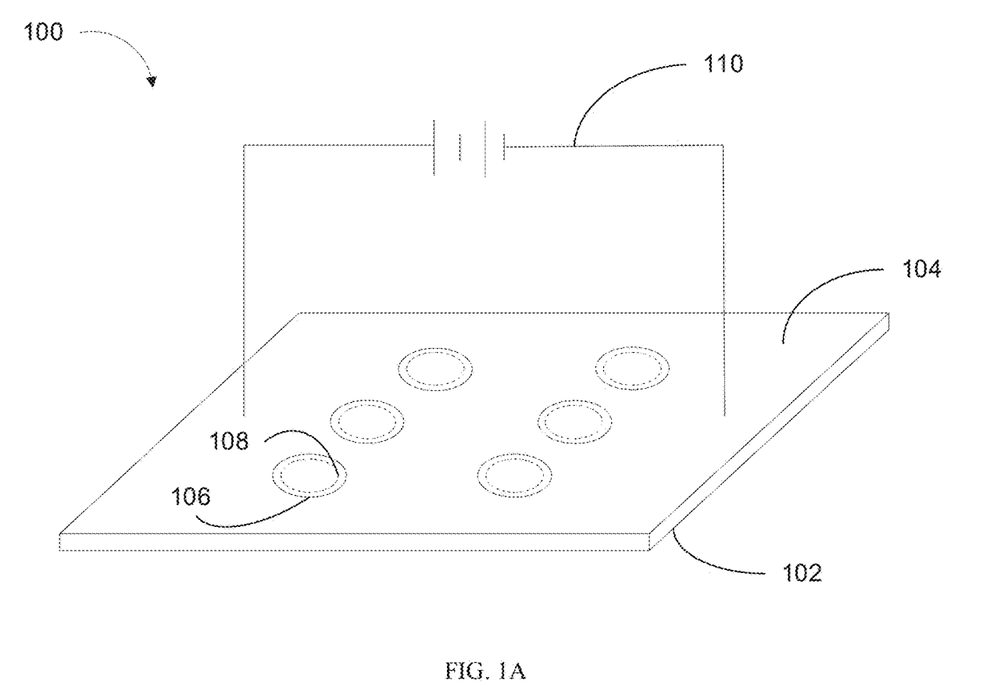
FIG. 1A illustrates an example electrical nanopore device including several nanopores on a substrate with an electrical stimulus, in accordance with some embodiments of the present disclosure.
Figure 1B:
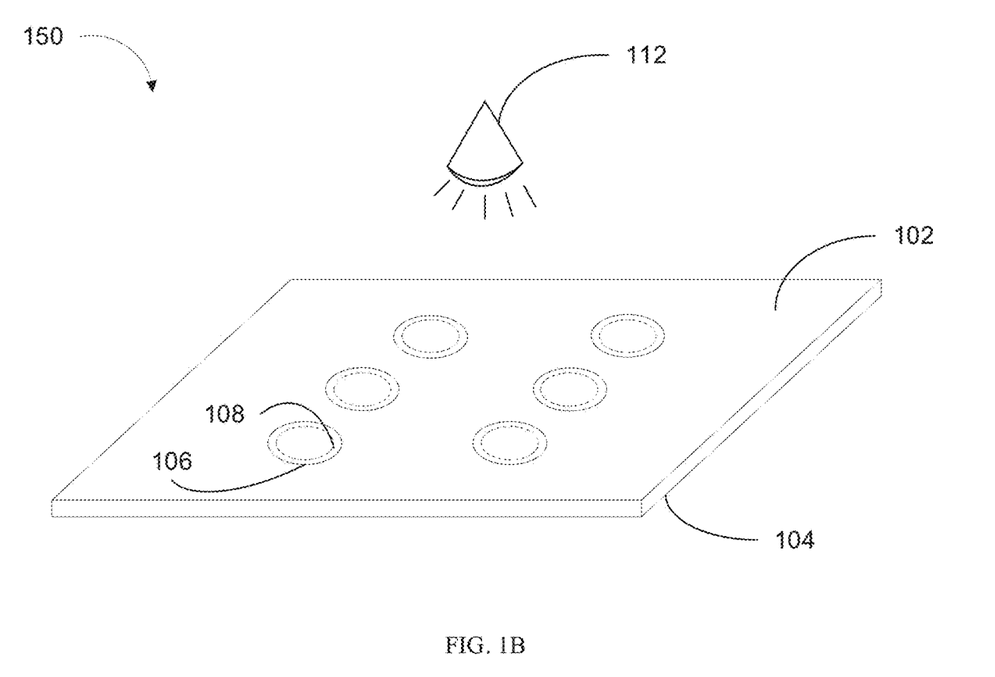
FIG. 1B illustrates an example optical nanopore device including several nanopores on a substrate with an optical stimulus, in accordance with some embodiments of the present disclosure.

Referring now to various embodiments of the disclosure in more detail, FIGS. 1A and 1B are representations of embodiments of a functional nanopore device generally labeled 100 and 150 respectively. FIGS. 1A and 1B provide illustrations of implementations and do not imply any limitation with regard to the environments in which different embodiments may be implemented. Many modifications of the depicted environment may be made by those skilled in the art without departing from the spirit and scope of the present disclosure.

Nanopore device 100 includes substrate 102, nanopore surface 104, first nanopore geometry 106, and second nanopore geometry 108.

Substrate 102 may be any material which can support a nanopore. Some examples include but are not limited to metals, semi-metals, polymers, silver doped polymers, and silicon-based materials. In some embodiments it is beneficial when substrate 102 is at least semi-conductive. In some embodiments, substrate 102 is a polymer that has been doped with a metal (i.e. silver) to make it conductive.

In various embodiments, nanopore surface 104 is attached to substrate 102 or is an upper surface of substrate 102. Nanopore surface 104 contains at least one nanopore. Nanopore surface 104 can be permanently attached to substrate 102 or may be removably attached to substrate 102. In some embodiments, substrate 102 can be a specified size and shape on which multiple versions of nanopore surface 104 can be removably attached.

First nanopore geometry 106 represents a nanopore of an initial geometry. Second nanopore geometry 108 shows a different nanopore geometry on nanopore surface 104. FIGS. 1A and 1B depict the first and second nanopore geometry as circles of varying diameter. However, in some embodiments the geometry may be in varying shapes and orientations. Furthermore, although FIGS. 1A and 1B show first diameter 106 as larger than second diameter 108, the opposite can likewise occur (e.g., second diameter 108 larger than first diameter 106) in various embodiments.

FIG. 1A also includes electrical stimulus 110. In some embodiments, electrical stimulus 110 is configured to provide an electrical stimulus to the first nanopore geometry 106 on nanopore surface 104. In these embodiments, electrical stimulus 110 creates an electromechanical response in the first nanopore geometry 106. In some embodiments, the electrical connection between electrical stimulus 110 and first nanopore geometry 106 is substrate 102.

Electrical stimulus 110 can be any device that transfers electrical energy to first nanopore geometry 106 and includes at least a power source electrically connected to the first nanopore geometry 106. The power source may be a battery, a generator, any connection to an electric power grid (i.e., standard 110V or 220V outlet), or any other power source known in the art. The electrical connection may be from wires, from the substrate 102 that is conductive, from the nanopore surface 104, or any other method known in the art.

In some embodiments, there is a single electrical stimulus 110 that is configured to tune all nanopores on nanopore surface 104. In some embodiments, each nanopore 106 has a distinct electrical stimulus 110. In some embodiments, there is a unique combination of electrical stimulus 110 devices for the nanopores on nanopore surface 104. The ratio or the numbers may be configured in any fashion.

FIG. 1B includes optical stimulus 112. The optical stimulus 112 can be any device that emits optical energy including but not limited to a light emitting diode ("LED"), a laser, an incandescent bulb, a fluorescent bulb, or any other type of device known in the art. Optical stimulus 112 can emit light in one or more of the ultraviolet, visible, infrared, microwave, X-ray, gamma ray, or other areas of the electromagnetic spectrum. In some embodiments, optical stimulus 112 is configured to create an opto-mechanical response in the first nanopore geometry 106.

In some embodiments, there is a single optical stimulus 112 configured to stimulate all nanopores on nanopore surface 104. In some embodiments, there is an individual optical stimulus 112 for each individual nanopore. In some embodiments, there is a unique combination of optical stimulus 112 devices for the number nanopores. The ratio or the numbers may be configured in any fashion.

Although six nanopores are shown in FIGS. 1A and 1B, more are fewer nanopores are possible in various embodiments. Furthermore, a circuit associated with resistive pulse sensing is not shown for clarity in FIGS. 1A and 1B. However, such as circuit can exist in some embodiments.

Figure 2A:
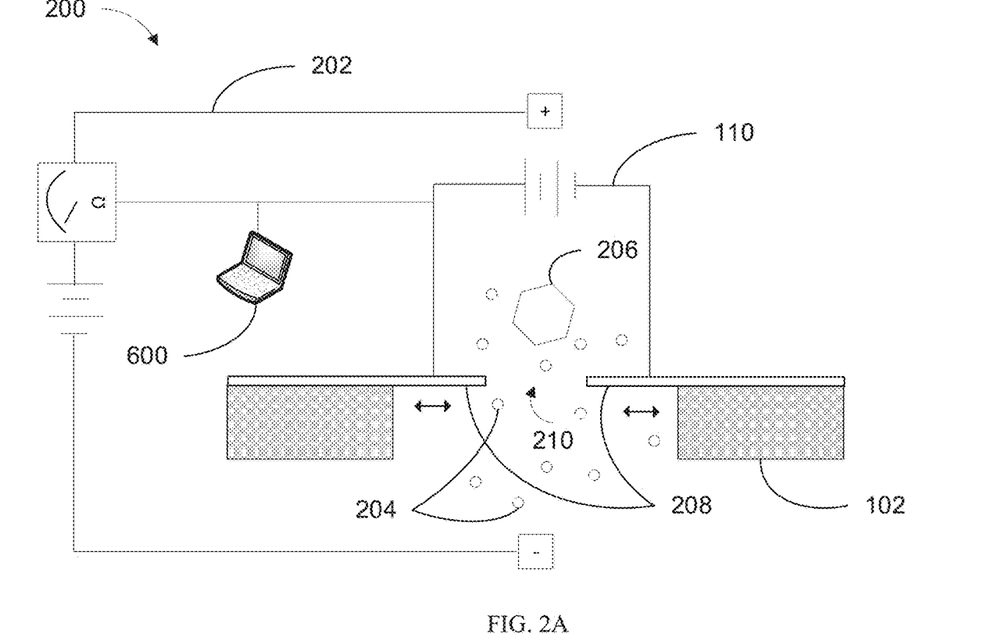
FIG. 2A illustrates a profile view of a graphene-based nanopore device, in accordance with some embodiments of the present disclosure.

FIG. 2A depicts the profile view of an embodiment of a nanopore device 200, which in some embodiments is consistent with nanopore device 100 of FIG. 1A. Nanopore device 200 includes a substrate 102, an electrical stimulus 110, sensing circuit 202, a particle 206, graphene layer 208, graphene nanopore 210, and characterization manager 600.

Substrate 102 in FIG. 2A can be consistent with substrate 102 in FIGS. 1A and 1B. Substrate 102 provides support for and a location on which to place a nanopore, such as graphene nanopore 210. Substrate 102 can be metal, plastic, or any other material capable of supporting a nanopore, including the materials discussed above regarding substrate 102 in FIGS. 1A and 1B.

Electrical stimulus 110 provides electrical power to create an electromechanical response in graphene layer 208. Electrical stimulus 110 can be configured in any fashion to provide the desired response as previously described with respect to FIGS. 1A and 1B.

Sensing circuit 202 provides a path for current to flow through the graphene nanopore 210. In some embodiments, sensing circuit 202 provides a path for current flow from the entrance of graphene nanopore 210 to the exit of graphene nanopore 210. Sensing circuit 202 includes at least a current source, a conductor, and at least one detector. In some embodiments the detector can be chosen from a voltage meter, ammeter, or resistance meter. The current source provides for a voltage to cause current flow. The conductor provides a path for the current flow from the current source to the inlet side of the nanopore, and a return from the exit side of the nanopore. The circuit is completed by electrolyte 204.

Electrolyte 204 is a conducting fluid in which nanopore device 200 is submerged. In some embodiments, electrolyte 204 is capable of carrying sufficient current to render a reading on the detector of sensing circuit 202. In some embodiments, electrolyte 204 may also have particle 206 dispersed throughout the fluid. For purposes of this application, submerged can mean that the nanopore device 200 and the conductive fluid containing electrolyte 204 and particle 206 are configured such that the conductive fluid comes in contact with the nanopore (e.g., graphene nanopore 210) such the it can traverse the nanopore with any suspended particles (e.g., particle 206).

Particle 206 represents a particle in a sample that can be detected using nanopore device 200. Particle 206 may be any type of particle that is suspended in a fluid. This includes, but is not limited to, individual atoms, molecules, compounds, ions, viruses, biologics, minerals, and the like. In some embodiments, there is a single type of particle 206. In some embodiments, there are multiple distinct particles that are collectively referred to as particle 206. In FIG. 2A, particle 206 represents any particle traversing graphene nanopore 210 other than electrolyte 204.

Graphene layer 208 includes one or more layers of graphene distributed across substrate 102. In some embodiments, graphene layer 208 is comprised of a single layer of graphene. In other embodiments, graphene layer 208 includes two or more layers of graphene. In some embodiments, graphene layer 208 is configured to respond to electrical stimulus 110 as depicted by the double-sided arrows (e.g., expanding and contracting to cause changes in graphene nanopore 210).

Graphene is an allotrope of carbon consisting of a single layer of carbon atoms arranged in a hexagonal lattice. The hexagonal lattice allows graphene to form large, essentially two-dimensional (a single layer of carbon atoms thick) sheets. It is the basic structural element of many other allotropes of carbon such as graphite, diamonds, fullerenes, and carbon nanotubes. Carbon based materials, such as graphene, demonstrate exceptional actuation properties making them ideal to create a tunable nanopore.

Graphene nanopore 210 is an opening in the graphene layer 208 that provides a path for particle 206 to traverse through graphene layer 208. In some embodiments, graphene nanopore 210 can be formed by laying sheets of graphene on substrate 102 in a pattern to leave a nanopore between separate graphene sheets in the same layer. In some embodiments, the graphene nanopore 210 can be formed by targeted selective doping of graphene layer 208 to control local and global properties. In some embodiments, graphene nanopore 210 is formed by machining or etching a graphene layer previously placed on substrate 102.

The thickness of graphene nanopore 210 is controlled by the number of layers of graphene. In some embodiments, graphene nanopore 210 is the thickness of a single graphene layer 208. In other embodiments, graphene nanopore 210 is the thickness of a multi-layered graphene layer 208. In some embodiments, graphene nanopore 210 is configured such that at least one additional probe can be used to obtain additional information about particle 206 while it is traversing graphene nanopore 210. The probe can be any device known in the art used to characterize or determine properties of particles.

In some embodiments, graphene nanopore 210 can be configured to capture particle 206. In these embodiments, sensing circuit 202 determines particle 206 has traversed graphene nanopore 210, causing electrical stimulus 110 to reduce the opening in graphene nanopore 210 such that particle 206 is unable to traverse graphene nanopore 210 in the reverse direction. In some embodiments, sensing circuit 202 determines particle 206 is in the process of traversing graphene nanopore 210 and causes electrical stimulus 110 to actuate graphene layer 208 such that graphene nanopore 210 clamps on particle 206 preventing further movement of particle 206. In some embodiments, particle 206 is captured in a void space between graphene layer 208 and substrate 102, where the void space is configured to retain particle 206.

Characterization manager 600 is a device that can provide information to, and receive information from, both sensing circuit 202 and electrical stimulus 110. In some embodiments, characterization manager 600 is electrically connected to sensing circuit 202 and/or electrical stimulus 110. In some embodiments, characterization manager 600 can actuate electrical stimulus 110. In some embodiments, characterization manager 600 receives data from electrical stimulus to determine the size of graphene nanopore 210. In some embodiments, characterization manager 600 records all stimuli that are applied to graphene nanopore 210 and uses the recorded information to determine the current nanopore geometry. In some embodiments, characterization manager 600 electrically connects sensing circuit 202 to electrical stimulus 110. Characterization manager 600 will be discussed in more detail below with regard to FIG. 6.

Figure 2B:
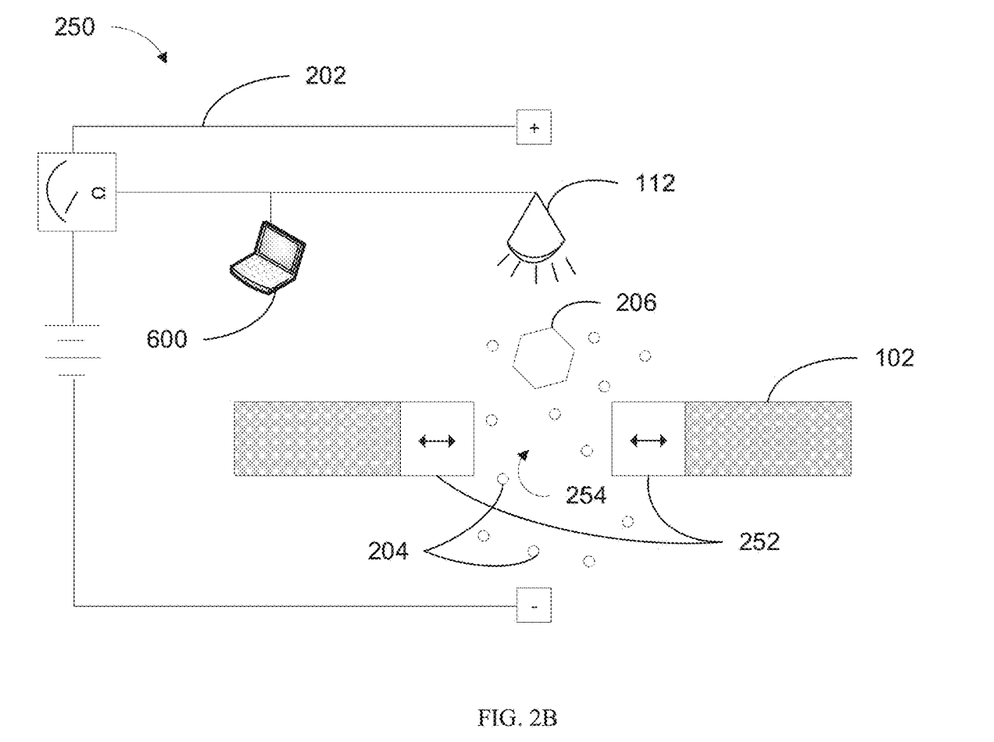
FIG. 2B illustrates a profile view of a carbon nanotube-based nanopore device, in accordance with some embodiments of the present disclosure.

FIG. 2B depicts an embodiment of a side profile of a nanopore device 250, which in some embodiments is consistent with nanopore device 150 of FIG. 1B. Nanopore device 250 includes substrate 102, optical stimulus 112, sensing circuit 202, particle 206, carbon nanotube 252, and carbon nanotube nanopore 254.

Substrate 102, in FIG. 2B can be consistent with substrate 102 in FIGS. 1A, 1B, and 2A. Substrate 102 provides support for and a location on which to place the carbon nanotube nanopore 254. Substrate 102 can be metal, plastic, silver doped polymers, silicon-based materials, or any other material capable of supporting the carbon nanotube nanopore 254.

Optical stimulus 112, provides electromagnetic radiation to create an opto-mechanical response in carbon nanotube 252. Optical stimulus 112 can be configured in any fashion as to provide the desired response as previously disclosed.

Sensing circuit 202 provides a path for current to flow through nanopore device 250. In some embodiments, sensing circuit 202 provides a path for current flow from the entrance of carbon nanotube nanopore 254 to the exit of carbon nanotube nanopore 254. Sensing circuit 202 of FIG. 2B can be consistent with sensing circuit 202 of FIG. 2A.

Electrolyte 204 is a conducting fluid in which nanopore device 250 is submerged. In some embodiments, electrolyte 204 is capable of carrying sufficient current to render a reading on the detector of sensing circuit 202. In some embodiments, electrolyte 204 may also have particle 206 dispersed throughout the fluid. Electrolyte 204 of FIG. 2B can be consistent with electrolyte 204 of FIG. 2A.

Particle 206 represents a particle in a sample that can be characterized. Particle 206 may be any type of particle that is suspended in a liquid. This includes but is not limited to individual atoms, molecules, compounds, ions, viruses, biologics, minerals, and the like. In some embodiments, there is a single type of particle 206. In some embodiments, there are multiple distinct particles that are collectively referred to as particle 206. In FIG. 2B, particle 206 represents any particle traversing nanopore system 250 other than electrolyte 204.

Carbon nanotube 252 includes one or more carbon nanotubes selectively attached to substrate 102. In some embodiments, carbon nanotube 252 is a single nanotube. In some embodiments, carbon nanotube 252 includes two or more individual nanotubes. In some embodiments, carbon nanotube 252 is configured to respond to optical stimulus 112 and move as depicted by the double-sided arrows in FIG. 2B.

Carbon nanotube 252 is an allotrope of carbon with a cylindrical nanostructure. In carbon nanotube 252, the atoms are arranged in a hexagonal fashion, similar to graphene, except the two edges of a graphene sheet bond together forming a cylinder with hollow space (e.g., a tube) through the center. Carbon based materials, such as carbon nanotube 252, demonstrate exceptional actuation properties making them ideal to create a tunable nanopore. Carbon nanotube 252 can be either of two main types of nanotubes, single-walled nanotubes ("SWNT") and multi walled nanotubes ("MWNT"). The surface charge of MWNT is effectively zero, making electrophoretic transport simple. Electrophoretic transport is a method of moving particles dispersed in a fluid under the influence of a spatially uniform electric field. Electrophoretic transport is frequently used while utilizing resistive pulse sensing.

Carbon nanotube nanopore 254 is an opening in carbon nanotube 252 that provides a path for particle 206 to traverse through carbon nanotube 252. In some embodiments, carbon nanotube nanopore 254 is formed by selectively attaching carbon nanotube 252 on substrate 102. In some embodiments the carbon nanotube nanopore 254 is formed by attaching carbon nanotube 252 to any portion of substrate 102. In some embodiments, carbon nanotube nanopore 254 is formed by attaching carbon nanotube 252 to an edge of substrate 102. In some embodiments, carbon nanotube nanopore 254 is formed by attaching carbon nanotube 252 to substrate 102 in a location where carbon nanotube nanopore 254 is aligned with a pore in substrate 102, to allow particle 206 to fully traverse carbon nanotube nanopore 254.

The length of carbon nanotube nanopore 254 is controlled by the length of carbon nanotube 252. In some embodiments, carbon nanotube nanopore 254 is configured such that at least one additional probe can be used to obtain additional information about particle 206 while it is traversing carbon nanotube nanopore 254. The probe can be any device known in the art used to characterize or determine properties of particles.

Characterization manager 600 is a device that can provide information to and receive information from both sensing circuit 202 and optical stimulus 112. In some embodiments, characterization manager 600 is electrically connected to optical stimulus 112 and sensing circuit 202. In some embodiments, characterization manager 600 records the time and type of stimulus actuated and uses the recorded information to determine the geometry of carbon nanotube nanopore 254. In some embodiments, characterization manager 600 actuates optical stimulus 112. In some embodiments, characterization manager 600 electrically connects sensing circuit 202 to optical stimulus 112. Characterization manager 600 is discussed in more detail below.

The elements depicted in the nanopore systems of FIGS. 2A and 2B are not mutually exclusive. In some embodiments, electrical stimulus 110 can be paired with carbon nanotube 252 to create carbon nanotube nanopore 254. In some embodiments optical stimulus 112 can be paired with graphene layer 208 to create graphene nanopore 210.

FIGS. 3A-3F depict a nanopore device progressing through a series of steps in which molecules of two different sizes are characterized. FIGS. 3A-3F include substrate 102, electrical stimulus 110, sensing circuit 202, electrolyte 204, carbon nanotube 252, and carbon nanotube nanopore 254. In other embodiments the same process could be completed with graphene layer 208 and graphene nanopore 210 substituted for carbon nanotube 252 and carbon nanotube nanopore 254 and/or with optical stimulus 112 substituted for electrical stimulus 110.

Figure 3A:
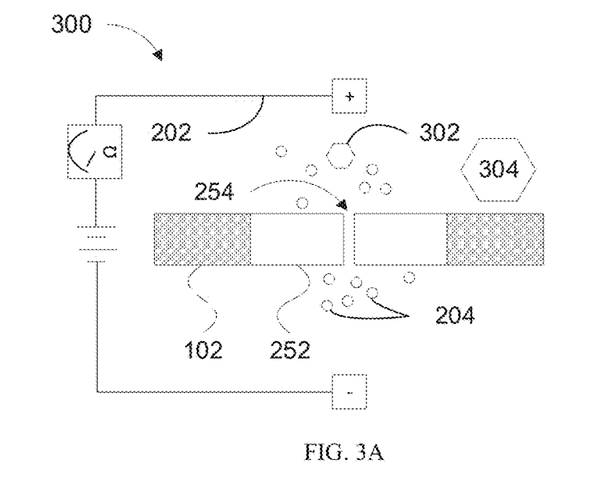
FIG. 3A illustrates a block diagram of a carbon nanotube nanopore device where no molecule can traverse the nanopore, in accordance with some embodiments of the present disclosure.

FIG. 3A depicts a nanopore device 300 where the initial carbon nanotube nanopore 254 is sufficiently small such that no particle can traverse nanopore device 300. FIG. 3A includes previously disclosed elements substrate 102, sensing circuit 202, electrolyte 204, carbon nanotube 252, carbon nanotube nanopore 254. FIG. 3A also includes first molecule 302, and second molecule 304.

First molecule 302 and second molecule 304 can be consistent with particle 206 of FIGS. 2A and 2B. In this embodiment, first molecule 302 is smaller than second molecule 304, where first molecule 302 and second molecule 304 together make up a polydisperse sample that may benefit from molecular characterization.

The area portrayed by carbon nanotube 252 is not necessarily a representation of the actual or relative size of the carbon nanotube. Rather, it portrays an area sufficiently small so as to prevent first molecule 302, second molecule 304, or other particles from traversing through that portion of nanopore device 300.

Figure 3B:
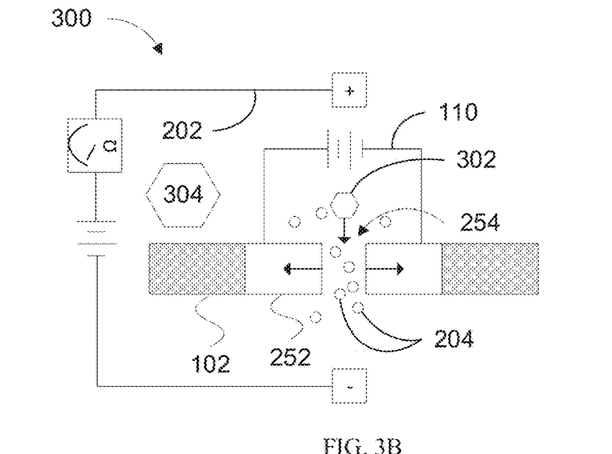
FIG. 3B illustrates an increase in the size of a nanopore, in accordance with some embodiments of the present disclosure.

FIG. 3B depicts a carbon nanotube nanopore device 300 while the nanopore geometry is changing such that molecule 302 can traverse carbon nanotube nanopore 254. Carbon nanotube nanopore 254 can change as a result of a stimulus applied from electrical stimulus 110. Nanopore device 300 includes the previously disclosed elements: substrate 102, electrical stimulus 110, sensing circuit 202, electrolyte 204, carbon nanotube 252, carbon nanotube nanopore 254, first molecule 302, and second molecule 304.

Figure 3C:
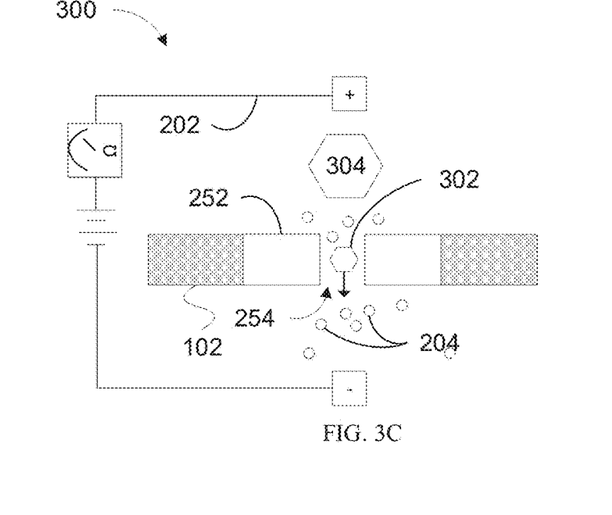
FIG. 3C illustrates a first molecule transiting through the nanopore, in accordance with some embodiments of the present disclosure.

FIG. 3C depicts nanopore device 300 while first molecule 302 is traversing carbon nanotube nanopore 254. Nanopore device 300 includes the previously disclosed elements: substrate 102, sensing circuit 202, electrolyte 204, carbon nanotube 252, carbon nanotube nanopore 254, first molecule 302, and second molecule 304.

While first molecule 302 is traversing carbon nanotube nanopore 254, it displaces a portion of electrolyte 204 from the carbon nanotube nanopore 254. This creates an interruption in the current flow through the carbon nanotube nanopore 254 resulting in an increase in voltage, or an increase in resistance across the pore. The change in voltage (or other electrical property) is detectable, and correlates to the size of first molecule 302 relative to the size of carbon nanotube nanopore 254. The size information can be compared against known data in order to characterize first molecule 302. At this point, carbon nanotube nanopore 254 is sufficiently small that second molecule 304 cannot traverse across nanopore device 300.

Figure 3D:
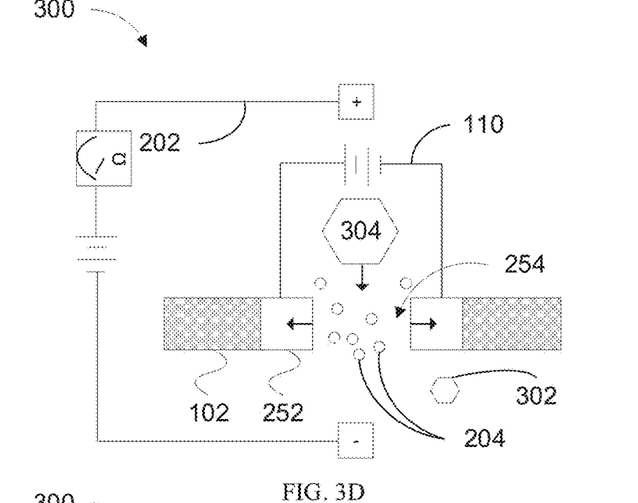
FIG. 3D illustrates a second increase in the size of the nanopore, in accordance with some embodiments of the present disclosure.

FIG. 3D depicts carbon nanotube nanopore device 300 after another electrical stimulus 110 has caused another electromechanical response in carbon nanotube nanopore 254 so that carbon nanotube nanopore 254 changes size (e.g., expands in diameter). Nanopore device 300 includes the previously disclosed elements: substrate 102, electrical stimulus 110, sensing circuit 202, electrolyte 204, carbon nanotube 252, carbon nanotube nanopore 254, first molecule 302, and second molecule 304.

The geometry of carbon nanotube nanopore 254 is changed in response to receiving electrical stimulus 110 such that the larger second molecule 304 is able to traverse nanopore device 300.

Figure 3E:
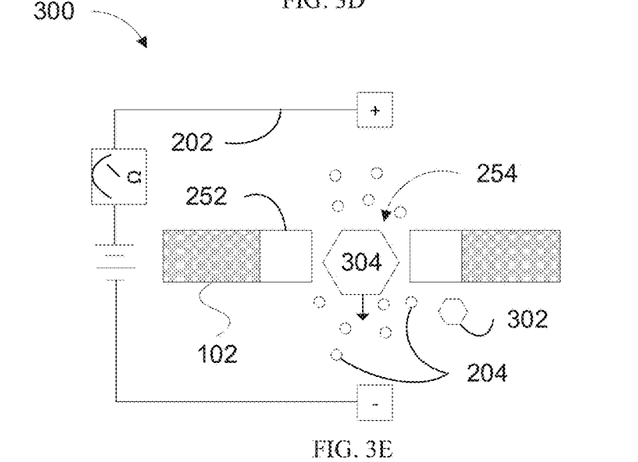
FIG. 3E illustrates a second, larger, molecule traversing through the nanopore, in accordance with some embodiments of the present disclosure.

FIG. 3E depicts carbon nanotube nanopore device 300 while second molecule 304 is traversing carbon nanotube nanopore 254. Nanopore device 300 includes the previously disclosed elements: substrate 102, sensing circuit 202, electrolyte 204, carbon nanotube 252, carbon nanotube nanopore 254, first molecule 302, and second molecule 304.

While second molecule 304 is traversing carbon nanotube nanopore 254, it displaces a portion of electrolyte 204 from the carbon nanotube nanopore 254. This creates an interruption in the current flow through the carbon nanotube nanopore 254 resulting in an increase in voltage, or an increase in resistance across the pore. The change in voltage (or other electrical property) is detectable, and the change in voltage correlates to the size of second molecule 304 relative to the size of carbon nanotube nanopore 254. The size information can be compared against known data in order to characterize the second molecule 302.

Figure 3F:
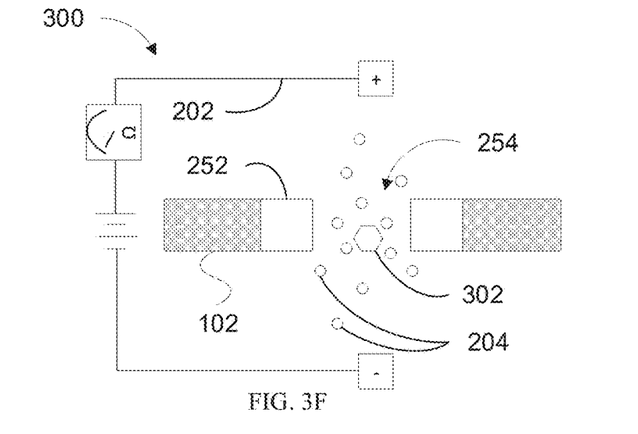
FIG. 3F illustrates the smaller molecule traversing through the nanopore, in accordance with some embodiments of the present disclosure.

FIG. 3F depicts carbon nanotube nanopore device 300 while first molecule 302 is traversing carbon nanotube nanopore 254. Nanopore device 300 includes the previously disclosed elements: substrate 102, sensing circuit 202, electrolyte 204, carbon nanotube 252, carbon nanotube nanopore 254, and first molecule 302.

FIG. 3F is included to demonstrate the usefulness of an in situ tunable nanopore. In FIG. 3F, first molecule 302 is traversing carbon nanotube nanopore 254, however, there is still sufficient electrolyte 204 in the nanopore to maintain current flow at an approximately stable level. In this scenario, the change in voltage would be insufficient to detect and then characterize first molecule 302. This is useful since first molecule 302 was previously characterized in FIG. 3C.

Figure 4:
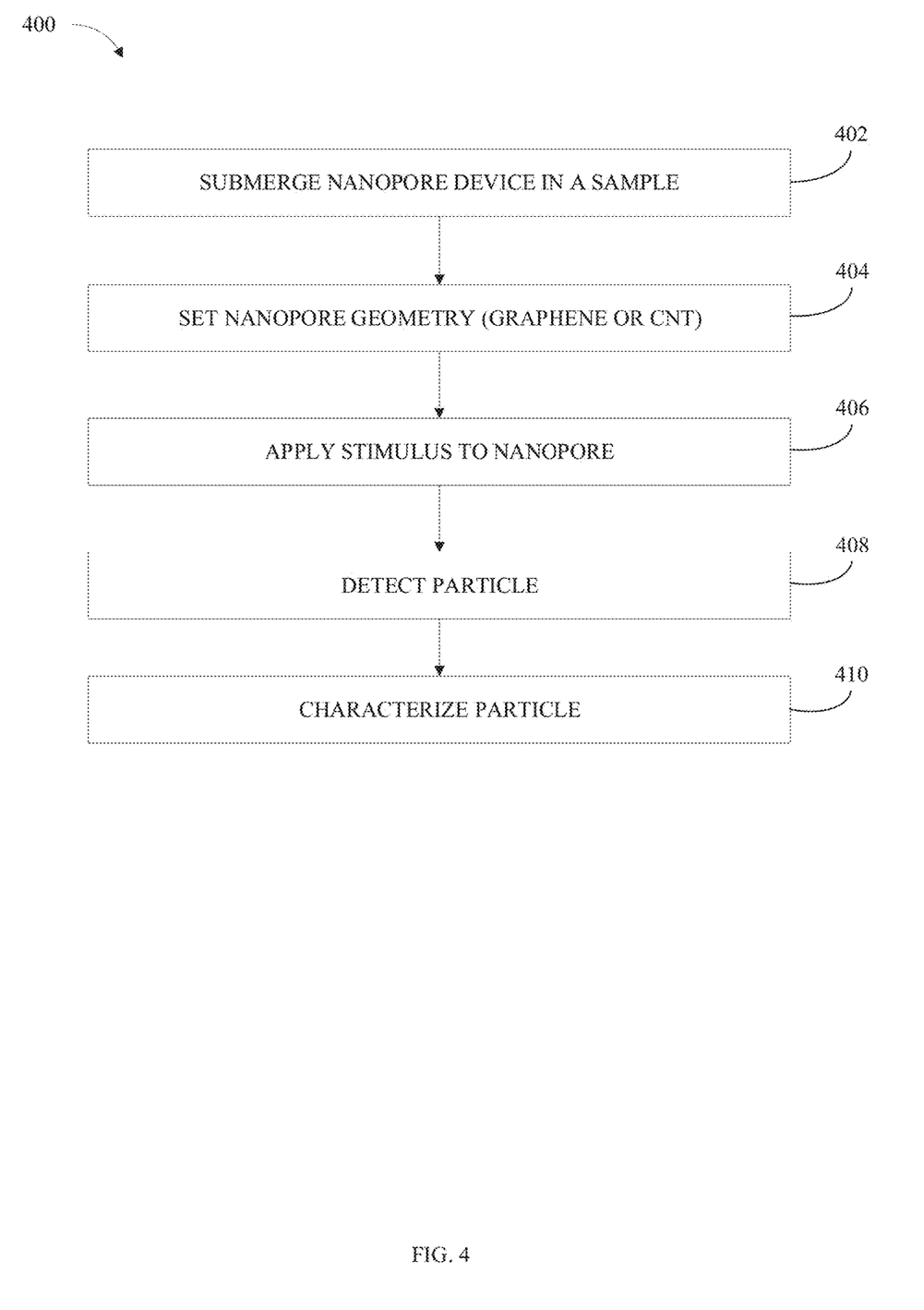
FIG. 4 illustrates a flowchart of an example method for characterizing a polydisperse sample using a nanopore device, in accordance with some embodiments of the present disclosure.

FIG. 4 is a flowchart depicting a method 400 for detecting a particle using a nanopore device, in accordance with some embodiments of the present disclosure. It should be appreciated that embodiments of this disclosure provide for in situ tunable nanopores capable of characterizing particles dispersed in a fluid. FIG. 4 provides an illustration of one implementation and does not imply any limitations with regard to the environments in which different embodiments may be implemented. Method 400 can include more or fewer operations than those operations that are explicitly depicted. Method 400 can include operations in different orders than those orders depicted. Likewise, the method 400 can include operations that occur simultaneously rather than sequentially. Many modifications to the depicted method may be made by those skilled in the art without departing from the spirit and scope of the present disclosure.

At step 402, a nanopore device is submerged in a sample to be characterized. The nanopore device and the fluid can be configured such that the fluid and the particles suspended in the fluid can traverse a nanopore of the nanopore device. In some embodiments the fluid is an electrolyte (e.g., electrolyte 204). In some embodiments, the nanopore device is previously assembled with a tank configured to hold the fluid. In these embodiments, the fluid can be added to the tank to submerge the nanopore device. In some embodiments, the nanopore device is portable, and is lowered into a separate container that contains the fluid.

At step 404, a first nanopore geometry is set. In some embodiments, the geometry is set by molecular characterization manager 600. In some embodiments, the first geometry is set based on a pre-determined geometry. In some embodiments, the first geometry is set based on an algorithm. In some embodiments, the first geometry is set by a the nanopore device. In some embodiments, the first nanopore geometry can be a circle of a first diameter. In some embodiments, the first nanopore geometry can be a rectangular shape. In some embodiments, the first nanopore geometry can be set to a size useful for identifying a known particle (such a technique may be useful for determining if a specific particle is present in the fluid).

In some embodiments, the first nanopore geometry can be set as a three-dimensional geometry. In some embodiments, the first nanopore geometry is set sufficiently small such that no particle can traverse the nanopore. Such a technique may be useful when the particle to be characterized is unknown.

In some embodiments, the nanopore can be graphene nanopore 210. In some embodiments, the nanopore can be carbon nanotube nanopore 254.

At step 406, a stimulus is applied to the nanopore. In some embodiments the stimulus causes a response in the nanopore resulting in a second nanopore geometry. In some embodiments, the second nanopore geometry can be a circle of a second diameter. In some embodiments, the second nanopore geometry can be a rectangular shape having a different area than the first nanopore geometry. In some embodiments, the second geometry can be a three-dimensional geometry of different volume than the first three-dimensional geometry.

The stimulus can be electrical stimulus 110 or optical stimulus 112. In some embodiments, the stimulus can be applied for a set period of time. In some embodiments, the stimulus can be applied until the nanopore obtains the second nanopore geometry. In some embodiments, the stimulus can be applied until a particle is detected. In some embodiments, the stimulus can be applied according to a directed search algorithm (as discussed in more detail hereinafter).

In step 408, the nanopore device detects a particle. The detection occurs when the particle is traversing the nanopore and displaces a sufficient amount of a conductive fluid (e.g., electrolyte 204) to interrupt current flow through the pore. The current flow interruption can be detected by a sensing circuit (e.g., sensing circuit 202).

In step 410, the nanopore device characterizes the particle. In some embodiments the nanopore device is electrically connected to a characterization manager (e.g., characterization manager 600). The characterization manager can send signals to, and receive signals from, the nanopore device. The signals can start and stop the stimulus (e.g., electrical stimulus 110 or optical stimulus 112).

The particle can be characterized by the characterization manager by comparing the size of the nanopore against the change in current flow across the nanopore to determine one or more properties of the particle. In these embodiments, one of the properties determined is the size of the particle. In some embodiments, the characterization manager uses the duration of the change in current as a factor in determining the properties of the particle. In some embodiments, the characterization manager compares the properties against known particle information to characterize the particle. The known information can be generally all information known about all chemicals and molecules, or information known about other particles in the sample. This information can be stored in the characterization manager, or accessible by the characterization manager via a network. Characterization manager will be discussed in further detail in relation to FIG. 6.

Figure 5:
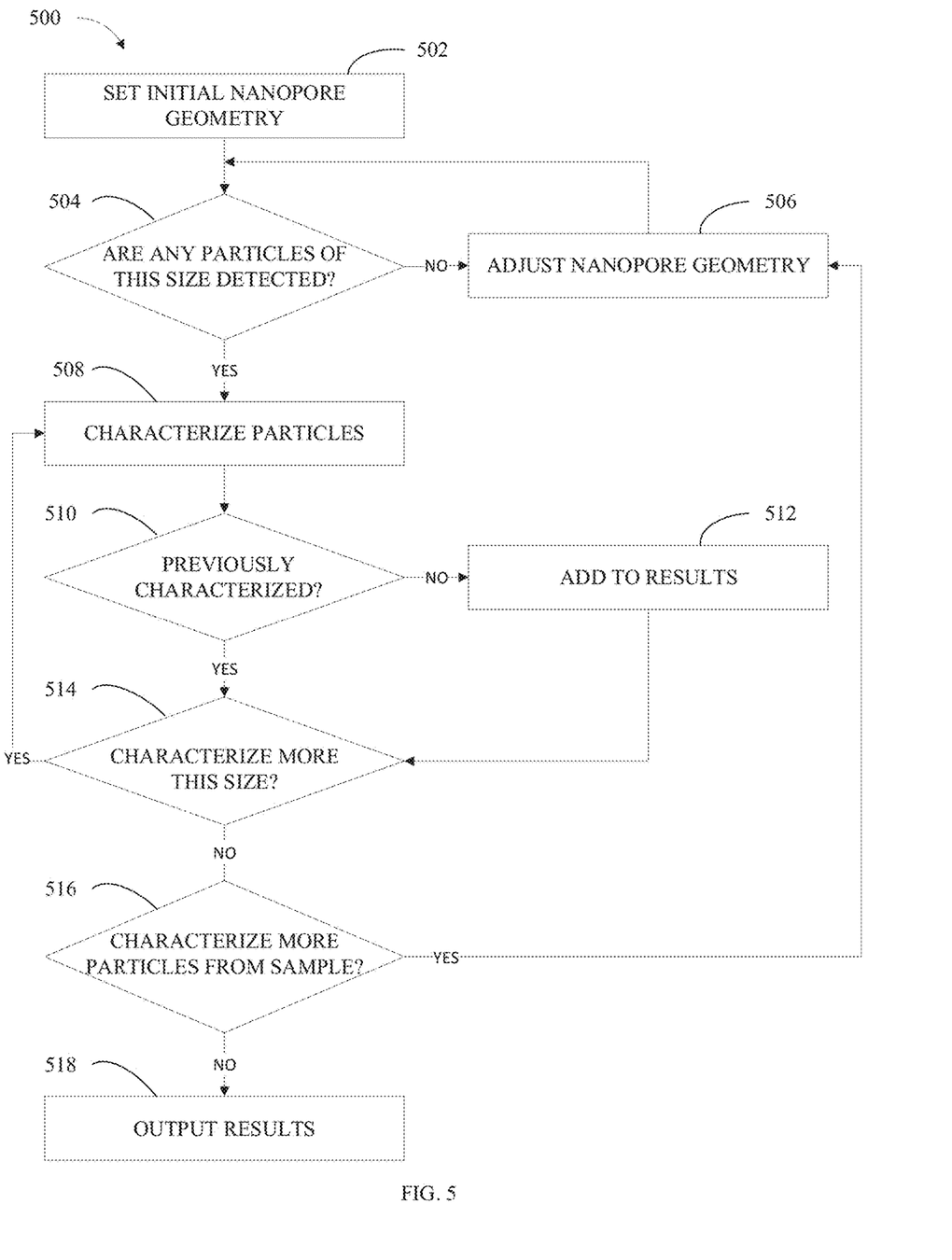
FIG. 5 illustrates a flowchart of an example method for characterizing a polydisperse sample using a nanopore device, in accordance with some embodiments of the present disclosure.

FIG. 5 is a flowchart depicting a method 500 for detecting and characterizing multiple particles in a polydisperse sample using a nanopore device, in accordance with embodiments of the present disclosure. In some embodiments, the method 500 adds additional detail to method 400. Method 500 can include more or fewer operations than those operations that are explicitly depicted. Method 500 can include operations in different orders than those orders depicted. Likewise, the method 500 can include operations that occur simultaneously rather than sequentially. Many modifications to the depicted method may be made by those skilled in the art without departing from the spirit and scope of the present disclosure.

In step 502, an initial nanopore geometry is set. In some embodiments, the nanopore initial geometry is set based on the smallest potential particle that can be detected. In some embodiments, the initial geometry is set such that no particles can traverse the nanopore.

In some embodiments, the first nanopore geometry is a circle of a first diameter. In some embodiments, the first nanopore geometry is a rectangle. In some embodiments, the first nanopore geometry can be set at a geometry to identify a known particle. Such embodiments can be most effective when trying to determine if a specific particle is present in the fluid.

In some embodiments, the first nanopore geometry is set sufficiently small that no particle can traverse the pore. Such embodiments can be effective when the particle to be characterized is unknown or the size of the particle is unknown.

In step 504, the nanopore device determines if any particles have been detected at the initial nanopore geometry. The detection occurs as previously disclosed. If no particles are detected, then step 506 is performed (decision step "NO" branch). If a particle is detected, then step 508 is performed (decision step "YES" branch).

In step 506, the nanopore device adjusts the nanopore geometry. The adjustment is such that particles that could not be detected with the initial nanopore geometry, or with a previous nanopore geometry, can be detected with the subsequent nanopore geometry. In some embodiments, the adjustment results in a larger nanopore. In some embodiments, the adjustment results in a smaller nanopore (i.e. the nanopore is initially set at a larger geometry and is made smaller). In some embodiments, the new geometry is a circle of differing diameter than the initial nanopore geometry. In some embodiments, the subsequent geometry is a rectangle of different area than the initial nanopore geometry. In some embodiments, the subsequent geometry is a three-dimensional zone with differing volume than the initial nanopore geometry. When step 506 is completed, the method 500 returns to step 504 and again determines if any particles can be detected.

In step 508, the nanopore device characterizes the particle detected in step 504. The characterization occurs as previously disclosed. In some embodiments, the characterization is based on a change in current, voltage, and/or resistance across the nanopore in addition to geometry information (e.g., a nanopore diameter) of the nanopore.

In step 510, the nanopore device determines if the particle characterized in step 508 has previously been characterized in the current sample. In some embodiments, this occurs by comparing the properties of the particle against the properties of particles stored in the results. If the particle has not been previously characterized, then step 512 is performed (decision step "NO" branch). If the particle has been previously characterized, then step 514 is performed (decision step "YES" branch).

In step 512, the nanopore device adds the properties of the characterized molecule to the results. After the properties are added to the results, step 514 is performed. The results are a cache of information that the nanopore device has obtained about particles in the sample. It can be stored in any manner so long as it capable of being retrieved. In some embodiments, the results are stored in a characterization manager (e.g., characterization manager 600). In some embodiments, the nanopore device records all instances of characterizing any particle in the results. In some embodiments, one set of data for a unique particle is stored in the results. In some embodiments, the aggregate data of the total number of characterized particles can be used to determine additional properties of the polydisperse sample, such as concentrations, diffusion rates, surface charges, viscosity and other similar properties.

In step 514, the nanopore device determines if there are particles of a similar size that still need to be characterized. Said differently, it determines if the pore geometry should be adjusted. If there are more particles of similar size to be characterized, then the method 500 returns to step 508 (decision step "YES" branch). If there are no more particles of similar size to be characterized, then the process proceeds to step 516 (decision step "NO" branch).

In some embodiments, the nanopore device determines that no more particles of similar size need to be characterized after any particle of that size has been characterized. Thus, the nanopore geometry is adjusted after each characterization. In some embodiments, the nanopore device determines that no more particles of similar size need to be characterized after a pre-set number of particles are characterized. In some embodiments, the preset number can be a number of identical particles. In some embodiments, the preset number can be the number of different particles of relatively the same size.

In some embodiments, the nanopore device determines that no more particles of similar size need to be characterized based on the amount of time the nanopore has been set at its current geometry. In some embodiments, the time is measured from the most recent change in nanopore geometry. In such embodiments, the pore maintains a specific geometry for a specific period of time. In some embodiments, the time is measured from the time a first molecule traversed the nanopore. In some embodiments, the time is measured from the time that the first molecule is characterized. In some embodiments, the time is measured from the most recent characterization of a particle. In some embodiments, the time is measured from the most recent characterization of a unique particle.

In some embodiments, the nanopore device determines that no more particles of similar size need to be characterized based on a previously determined algorithm. In some embodiments, the algorithm is set based on looking for a specific class or set of particles. For example, consider a sample that may include particle 1 and particle 2, yet particle 1 and 2 are different sizes. The algorithm can set an initial geometry to detect and characterize particle 1. Once it has been determined particle 1 was present, the nanopore geometry is adjusted to detect and characterize particle 2. In some embodiments, the algorithm can select a size corresponding to particle 2 based on particle 2 having a probability of being associated with particle 1 above a threshold, and/or further based on information gained by confirming the presence or absence of particle 2 contributing to characterization of the sample.

In some embodiments, the algorithm is set to adjust through a series of nanopore geometries at specific times. In some embodiments, the algorithm may choose a subsequent geometry based on the identity of a previously characterized particle.

In step 516, the nanopore device determines if there are potentially more particles of a different size that still need to be characterized in the sample. Said differently, it determines if characterization of the entire sample is complete. If there are more particles of different size to be characterized, then the process returns to step 506 and adjusts the nanopore geometry (decision step "YES" branch). If there are no more particles of a different size to be characterized, then the process proceeds to step 518 (decision step "NO" branch).

Figure 6:
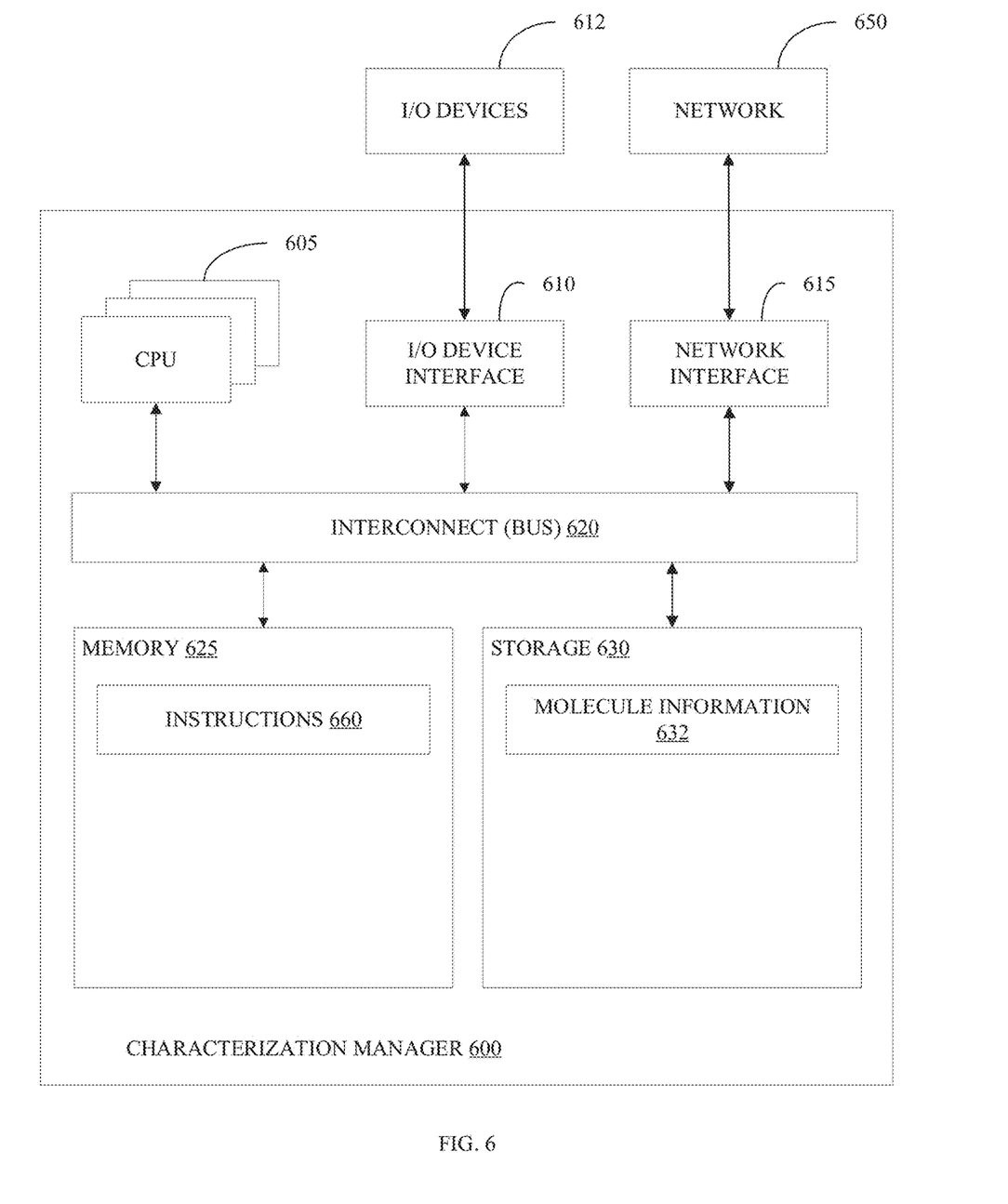
FIG. 6 illustrates a block diagram of an example characterization manager, in accordance with some embodiments of the present disclosure.

In step 518, the nanopore device outputs the results. In some embodiments the results are output via I/O devices (e.g., I/O devices 612).

FIG. 6 illustrates a block diagram of an example characterization manager 600 in accordance with some embodiments of the present disclosure. In various embodiments, characterization manager 600 can operate nanopore devices 100, 150, 200, 250, and/or 300 and perform the methods 400, and/or 500 as described in FIGS. 1-5. In some embodiments, characterization manager 600 provides instructions for any of the methods 400, and/or 500 of FIGS. 4-5 to a client machine such that the client machine executes the method, or a portion of the method, based on the instructions provided by the characterization manager 600.

The characterization manager 600 includes a memory 625, storage 630, an interconnect (e.g., BUS) 620, one or more CPUs 605 (also referred to as processors 605 herein), an I/O device interface 610, I/O devices 612, and a network interface 615.

Each CPU 605 retrieves and executes programming instructions stored in the memory 625 or storage 630. The interconnect 620 is used to move data, such as programming instructions, between the CPUs 605, I/O device interface 610, storage 630, network interface 615, and memory 625. The interconnect 620 can be implemented using one or more busses. The CPUs 605 can be a single CPU, multiple CPUs, or a single CPU having multiple processing cores in various embodiments. In some embodiments, a CPU 605 can be a digital signal processor (DSP). In some embodiments, CPU 605 includes one or more 3D integrated circuits (3DICs) (e.g., 3D wafer-level packaging (3DWLP), 3D interposer-based integration, 3D stacked ICs (3D-SICs), monolithic 3D ICs, 3D heterogeneous integration, 3D system in package (3DSiP), and/or package on package (PoP) CPU configurations). Memory 625 is generally included to be representative of a random-access memory (e.g., static random-access memory (SRAM), dynamic random-access memory (DRAM), or Flash). The storage 630 is generally included to be representative of a non-volatile memory, such as a hard disk drive, solid state device (SSD), removable memory cards, optical storage, or flash memory devices. In an alternative embodiment, the storage 630 can be replaced by storage area-network (SAN) devices, the cloud, or other devices connected to the characterization manager 600 via the I/O device interface 610 or a network 650 via the network interface 615.

In some embodiments, the memory 625 stores instructions 660 and the storage 630 stores molecule information 632. However, in various embodiments, the instructions 660, and molecule information 632 are stored partially in memory 625 and partially in storage 630, or they are stored entirely in memory 625 or entirely in storage 630, or they are accessed over a network 650 via the network interface 615.

Instructions 660 can be processor-executable instructions for performing any portion of, or all of, any of the methods 400 or 500 of FIGS. 4 and 5.

Molecule information 632 is a collection of information about particles. This information is catalogued in any convenient fashion to aid in characterization of particles. In some embodiments, molecule information 632 includes a list of molecules and their associated properties. Some of the properties include size, diffusion coefficients, and surface charge information. It can include any property of molecules that will assist in characterizing unknown particles in a sample. In some embodiments, the properties of a particle detected is compared against known properties to determine the identity of the particle.

In various embodiments, the I/O devices 612 include an interface capable of presenting information and receiving input. For example, I/O devices 612 can present information to a user interacting with characterization manager 600 and receive input from the user.

Characterization manager 600 is connected to the network 650 via the network interface 615. Network 650 can comprise a physical, wireless, cellular, or different network.

Embodiments of the present disclosure can be a system, a method, and/or a computer program product at any possible technical detail level of integration. The computer program product can include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or subset of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While it is understood that the process software (e.g., any of the instructions stored in instructions 660 of FIG. 6 and/or any software configured to perform any subset of the methods described with respect to FIGS. 4-5) can be deployed by manually loading it directly in the client, server, and proxy computers via loading a storage medium such as a CD, DVD, etc., the process software can also be automatically or semi-automatically deployed into a computer system by sending the process software to a central server or a group of central servers. The process software is then downloaded into the client computers that will execute the process software. Alternatively, the process software is sent directly to the client system via e-mail. The process software is then either detached to a directory or loaded into a directory by executing a set of program instructions that detaches the process software into a directory. Another alternative is to send the process software directly to a directory on the client computer hard drive. When there are proxy servers, the process will select the proxy server code, determine on which computers to place the proxy servers' code, transmit the proxy server code, and then install the proxy server code on the proxy computer. The process software will be transmitted to the proxy server, and then it will be stored on the proxy server.

Embodiments of the present invention can also be delivered as part of a service engagement with a client corporation, nonprofit organization, government entity, internal organizational structure, or the like. These embodiments can include configuring a computer system to perform, and deploying software, hardware, and web services that implement, some or all of the methods described herein. These embodiments can also include analyzing the client's operations, creating recommendations responsive to the analysis, building systems that implement subsets of the recommendations, integrating the systems into existing processes and infrastructure, metering use of the systems, allocating expenses to users of the systems, and billing, invoicing (e.g., generating an invoice), or otherwise receiving payment for use of the systems.

What is claimed is:
1. A nanopore device comprising:
a supporting substrate submerged in a polydisperse sample;
at least one nanopore connected to the supporting substrate including a first nanopore, wherein each nanopore consists of a carbon nanotube having a first diameter, and the first nanopore is configured to receive a stimulus that causes a change in the first diameter of the first nanopore to a second diameter, wherein the stimulus is an electrical stimulus, and wherein the supporting substrate is conductive;
a device configured to provide the stimulus to the first nanopore, wherein the device configured to provide the stimulus is an electrical device;
an electrical circuit configured to measure an electrical property across the first nanopore and to detect a change in the electrical property when a molecule traverses the first nanopore; and
a characterization manager configured to:
identify the identity of a first molecule, based on a first change in the electrical property from the first molecule that traversing the first nanopore at the first diameter;
select the second diameter based on the identity of the first molecule;
determine there are no additional molecules of a size of the first molecule in the polydisperse sample to be characterized, wherein the stimulus to cause the change in the first diameter to the second diameter is in response to the size determination;
identify a second molecule, based on a second change in the electrical property from the second molecule traversing the first nanopore at the second diameter, wherein the second molecule is unable to traverse the first nanopore at the first diameter, and the first molecule and the second molecule are included in the polydisperse sample;
determine there are no more molecules in the polydisperse sample to be characterized; and
determine concentration of the first molecule and the second molecule in the polydisperse solution.
2. The nanopore device of claim 1, wherein the first diameter is configured to correspond to the first molecule.
3. The nanopore device of claim 1, wherein the supporting substrate comprises a silver loaded polymer.
4. The nanopore device of claim 1, wherein the second diameter is larger than the first diameter.
5. The nanopore device of claim 4, wherein the second diameter of the first nanopore is configured to correspond to a second molecule, wherein the second molecule is chemically unique from the first molecule.
6. The nanopore device of claim 1, wherein the device configured to provide the stimulus to the first nanopore is further configured to:
apply the stimulus in response to the identification of the identity of the first molecule; and
apply the stimulus until the second molecule traverses the first nanopore.
7. A nanopore device comprising:
a supporting substrate submerged in a polydisperse sample;
at least one nanopore connected to the supporting substrate including a first nanopore, wherein each nanopore consists of a carbon nanotube having a first diameter, and the first nanopore is configured to receive a stimulus that causes a change in the first diameter of the first nanopore to a second diameter, wherein the stimulus is an optical stimulus received from an optical device;
an electrical circuit configured to measure an electrical property across the first nanopore and to detect a change in the electrical property when a first molecule traverses the first nanopore.

* * * * *